US010463819B2

(12) United States Patent
Jourdain et al.

(10) Patent No.: US 10,463,819 B2
(45) Date of Patent: *Nov. 5, 2019

(54) LEAK DETERMINATION IN A BREATHING ASSISTANCE SYSTEM

(71) Applicant: Covidien LP, Boulder, CO (US)

(72) Inventors: Cedric Jourdain, Lons (FR); Olivier Bernadet, Laroin (FR)

(73) Assignee: Covidien LP, Mansfield, MA (US)

( * ) Notice: Subject to any disclaimer, the term of this patent is extended or adjusted under 35 U.S.C. 154(b) by 953 days.

This patent is subject to a terminal disclaimer.

(21) Appl. No.: 14/980,052

(22) Filed: Dec. 28, 2015

(65) Prior Publication Data

US 2016/0106938 A1    Apr. 21, 2016

Related U.S. Application Data

(63) Continuation of application No. 14/570,106, filed on Dec. 15, 2014, now Pat. No. 9,254,369, which is a
(Continued)

(51) Int. Cl.
*A61M 16/00* (2006.01)
*A61M 16/08* (2006.01)
(Continued)

(52) U.S. Cl.
CPC .... *A61M 16/0066* (2013.01); *A61M 16/0003* (2014.02); *A61M 16/0057* (2013.01);
(Continued)

(58) Field of Classification Search
CPC .............. A61M 16/0051; A61M 16/00; A61M 16/0057; A61M 2016/0021;
(Continued)

(56) References Cited

U.S. PATENT DOCUMENTS 4,752,089 A    6/1988 Carter
4,921,642 A    5/1990 LaTorraca
(Continued)

FOREIGN PATENT DOCUMENTS

EP    0425092 A1    5/1991
EP    0714670 A2    6/1996
(Continued)

OTHER PUBLICATIONS

7200 Series Ventilator, Options, and Accessories: Operator's Manual. Nellcor Puritan Bennett, Part No. 22300 A, Sep. 1990, pp. 1-196.
(Continued)

*Primary Examiner* — Steven O Douglas (57) ABSTRACT

Systems and methods for estimating a leak flow in a breathing assistance system including a ventilation device connected to a patient are provided. Data of a flow waveform indicating the flow of gas between the ventilation device and the patient is accessed. A specific portion of the flow waveform is identified, and a linear regression of the identified portion of the flow waveform is performed to determine an estimated leak flow in the breathing assistance system.

20 Claims, 4 Drawing Sheets

Related U.S. Application Data continuation of application No. 14/059,193, filed on Oct. 21, 2013, now Pat. No. 8,939,150, which is a continuation of application No. 12/769,876, filed on Apr. 29, 2010, now Pat. No. 8,707,952.

(60) Provisional application No. 61/303,093, filed on Feb. 10, 2010.

(51) Int. Cl.
   *A61M 16/04*     (2006.01)
   *A61M 16/06*     (2006.01)
   *A61M 16/20*     (2006.01)

(52) U.S. Cl.
   CPC ...... *A61M 16/0069* (2014.02); *A61M 16/026* (2017.08); *A61M 16/04* (2013.01); *A61M 16/0666* (2013.01); *A61M 16/0883* (2014.02); *A61M 16/20* (2013.01); *A61M 16/0063* (2014.02); *A61M 2016/003* (2013.01); *A61M 2016/0015* (2013.01); *A61M 2016/0021* (2013.01); *A61M 2016/0027* (2013.01); *A61M 2016/0033* (2013.01); *A61M 2205/15* (2013.01); *A61M 2205/3334* (2013.01); *A61M 2205/505* (2013.01); *A61M 2205/52* (2013.01)

(58) Field of Classification Search
   CPC ...... A61M 2016/0033; A61M 2205/15; A61M 2205/2205; A61M 2205/505; A61M 16/0069; A61M 16/0003; A61M 16/0883; A61M 16/04; A61M 16/0666; A61M 16/20; A61M 2016/0027; A61M 2205/23; A61M 16/0066; A61M 16/026; A61M 16/0063; A61M 2016/0015; A61M 2205/3334; A61M 2205/52
   See application file for complete search history.

(56) References Cited

U.S. PATENT DOCUMENTS

| | | |
|---|---|---|
| 4,954,799 A | 9/1990 | Kumar |
| 5,057,822 A | 10/1991 | Hoffman |
| 5,072,728 A | 12/1991 | Pasternack |
| 5,072,737 A | 12/1991 | Goulding |
| 5,148,802 A | 9/1992 | Sanders et al. |
| 5,150,291 A | 9/1992 | Cummings et al. |
| 5,161,525 A | 11/1992 | Kimm et al. |
| 5,237,987 A | 8/1993 | Anderson et al. |
| 5,239,995 A | 8/1993 | Estes et al. |
| 5,271,389 A | 12/1993 | Isaza et al. |
| 5,279,549 A | 1/1994 | Ranford |
| 5,299,568 A | 4/1994 | Forare et al. |
| 5,301,921 A | 4/1994 | Kumar |
| 5,313,937 A | 5/1994 | Zdrojkowski et al. |
| 5,319,540 A | 6/1994 | Isaza et al. |
| 5,325,861 A | 7/1994 | Goulding |
| 5,333,606 A | 8/1994 | Schneider et al. |
| 5,339,807 A | 8/1994 | Carter |
| 5,343,857 A | 9/1994 | Schneider et al. |
| 5,351,522 A | 10/1994 | Lura |
| 5,357,946 A | 10/1994 | Kee et al. |
| 5,368,019 A | 11/1994 | LaTorraca |
| 5,383,449 A | 1/1995 | Forare et al. |
| 5,385,142 A | 1/1995 | Brady et al. |
| 5,390,666 A | 2/1995 | Kimm et al. |
| 5,401,135 A | 3/1995 | Stoen et al. |
| 5,402,796 A | 4/1995 | Packer et al. |
| 5,407,174 A | 4/1995 | Kumar |
| 5,413,110 A | 5/1995 | Cummings et al. |
| 5,433,193 A | 7/1995 | Sanders et al. |
| 5,438,980 A | 8/1995 | Phillips |
| 5,443,075 A | 8/1995 | Holscher |
| 5,492,113 A | 2/1996 | Estes et al. |
| 5,503,146 A | 4/1996 | Froehlich et al. |
| 5,513,631 A | 5/1996 | McWilliams |
| 5,517,983 A | 5/1996 | Deighan et al. |
| 5,520,071 A | 5/1996 | Jones |
| 5,524,615 A | 6/1996 | Power |
| 5,531,221 A | 7/1996 | Power |
| 5,535,738 A | 7/1996 | Estes et al. |
| 5,542,415 A | 8/1996 | Brody |
| 5,544,674 A | 8/1996 | Kelly |
| 5,549,106 A | 8/1996 | Gruenke et al. |
| 5,551,418 A | 9/1996 | Estes et al. |
| 5,551,419 A | 9/1996 | Froehlich et al. |
| 5,555,880 A | 9/1996 | Winter et al. |
| 5,596,984 A | 1/1997 | O'Mahony et al. |
| 5,598,838 A | 2/1997 | Servidio et al. |
| 5,630,411 A | 5/1997 | Holscher |
| 5,632,269 A | 5/1997 | Zdrojkowski |
| 5,632,270 A | 5/1997 | O'Mahony et al. |
| 5,645,048 A | 7/1997 | Brodsky et al. |
| 5,645,053 A | 7/1997 | Remmers et al. |
| 5,660,171 A | 8/1997 | Kimm et al. |
| 5,664,560 A | 9/1997 | Merrick et al. |
| 5,664,562 A | 9/1997 | Bourdon |
| 5,671,767 A | 9/1997 | Kelly |
| 5,672,041 A | 9/1997 | Ringdahl et al. |
| 5,673,689 A | 10/1997 | Power |
| 5,715,812 A | 2/1998 | Deighan et al. |
| 5,762,480 A | 6/1998 | Adahan |
| 5,771,884 A | 6/1998 | Yarnall et al. |
| 5,791,339 A | 8/1998 | Winter |
| 5,794,615 A | 8/1998 | Estes |
| 5,794,986 A | 8/1998 | Gansel et al. |
| 5,803,065 A | 9/1998 | Zdrojkowski et al. |
| 5,813,399 A | 9/1998 | Isaza et al. |
| 5,823,187 A | 10/1998 | Estes et al. |
| 5,826,575 A | 10/1998 | Lall |
| 5,829,441 A | 11/1998 | Kidd et al. |
| 5,864,938 A | 2/1999 | Gansel et al. |
| 5,865,168 A | 2/1999 | Isaza |
| 5,881,717 A | 3/1999 | Isaza |
| 5,881,723 A | 3/1999 | Wallace et al. |
| 5,884,622 A | 3/1999 | Younes |
| 5,884,623 A | 3/1999 | Winter |
| 5,901,704 A | 5/1999 | Estes et al. |
| 5,904,141 A | 5/1999 | Estes et al. |
| 5,909,731 A | 6/1999 | O'Mahony et al. |
| 5,915,379 A | 6/1999 | Wallace et al. |
| 5,915,380 A | 6/1999 | Wallace et al. |
| 5,915,382 A | 6/1999 | Power |
| 5,918,597 A | 7/1999 | Jones et al. |
| 5,921,238 A | 7/1999 | Bourdon |
| 5,927,274 A | 7/1999 | Servidio et al. |
| 5,934,274 A | 8/1999 | Merrick et al. |
| 5,970,975 A | 10/1999 | Estes et al. |
| 6,024,089 A | 2/2000 | Wallace et al. |
| 6,029,664 A | 2/2000 | Zdrojkowski et al. |
| 6,041,780 A | 3/2000 | Richard et al. |
| 6,047,860 A | 4/2000 | Sanders |
| 6,055,981 A | 5/2000 | Laswick et al. |
| 6,076,523 A | 6/2000 | Jones et al. |
| 6,105,575 A | 8/2000 | Estes et al. |
| 6,116,240 A | 9/2000 | Merrick et al. |
| 6,116,464 A | 9/2000 | Sanders |
| 6,123,073 A | 9/2000 | Schlawin et al. |
| 6,135,106 A | 10/2000 | Dirks et al. |
| 6,142,150 A | 11/2000 | O'Mahony et al. |
| 6,152,129 A | 11/2000 | Berthon-Jones |
| 6,161,539 A | 12/2000 | Winter |
| 6,220,245 B1 | 4/2001 | Takabayashi et al. |
| 6,253,765 B1 | 7/2001 | Hognelid et al. |
| 6,257,234 B1 | 7/2001 | Sun |
| 6,269,812 B1 | 8/2001 | Wallace et al. |
| 6,273,444 B1 | 8/2001 | Power |
| 6,279,569 B1 | 8/2001 | Berthon-Jones |
| 6,283,119 B1 | 9/2001 | Bourdon |
| 6,286,508 B1 | 9/2001 | Remmers et al. |
| 6,305,372 B1 | 10/2001 | Servidio |
| 6,305,373 B1 | 10/2001 | Wallace et al. |

(56) References Cited

U.S. PATENT DOCUMENTS

| | | |
|---|---|---|
| 6,305,374 B1 | 10/2001 | Zdrojkowski et al. |
| 6,321,748 B1 | 11/2001 | O'Mahoney |
| 6,325,785 B1 | 12/2001 | Babkes et al. |
| 6,357,438 B1 | 3/2002 | Hansen |
| 6,360,741 B2 | 3/2002 | Trosehel |
| 6,360,745 B1 | 3/2002 | Wallace et al. |
| 6,369,838 B1 | 4/2002 | Wallace et al. |
| 6,412,483 B1 | 7/2002 | Jones et al. |
| 6,425,395 B1 | 7/2002 | Brewer et al. |
| 6,427,689 B1 | 8/2002 | Estes et al. |
| 6,439,229 B1 | 8/2002 | Du et al. |
| 6,467,478 B1 | 10/2002 | Merrick et al. |
| 6,484,719 B1 | 11/2002 | Berthon-Jones |
| 6,532,957 B2 | 3/2003 | Berthon-Jones |
| 6,536,432 B2 | 3/2003 | Trosehel |
| 6,539,940 B2 | 4/2003 | Zdrojkowski et al. |
| 6,546,930 B1 | 4/2003 | Emerson et al. |
| 6,550,478 B2 | 4/2003 | Remmers et al. |
| 6,553,991 B1 | 4/2003 | Isaza |
| 6,553,992 B1 | 4/2003 | Berthon-Jones et al. |
| 6,557,553 B1 | 5/2003 | Borrello |
| 6,571,795 B2 | 6/2003 | Bourdon |
| 6,575,163 B1 | 6/2003 | Berthon-Jones |
| 6,578,575 B1 | 6/2003 | Jonson |
| 6,609,517 B1 | 8/2003 | Estes et al. |
| 6,622,726 B1 | 9/2003 | Du |
| 6,626,175 B2 | 9/2003 | Jafari et al. |
| 6,629,527 B1 | 10/2003 | Estes et al. |
| 6,644,310 B1 | 11/2003 | Delache et al. |
| 6,659,101 B2 | 12/2003 | Berthon-Jones |
| 6,668,824 B1 | 12/2003 | Isaza et al. |
| 6,675,801 B2 | 1/2004 | Wallace et al. |
| 6,688,307 B2 | 2/2004 | Berthon-Jones |
| 6,718,974 B1 | 4/2004 | Moberg |
| 6,725,447 B1 | 4/2004 | Gilman et al. |
| 6,739,337 B2 | 5/2004 | Isaza |
| 6,752,150 B1 | 6/2004 | Remmers et al. |
| 6,755,193 B2 | 6/2004 | Berthon-Jones et al. |
| 6,761,167 B1 | 7/2004 | Nadjafizadeh et al. |
| 6,761,168 B1 | 7/2004 | Nadjafizadeh et al. |
| 6,810,876 B2 | 11/2004 | Berthon-Jones |
| 6,814,074 B1 | 11/2004 | Nadjafizadeh et al. |
| 6,823,866 B2 | 11/2004 | Jafari et al. |
| 6,866,040 B1 | 3/2005 | Bourdon |
| 6,910,480 B1 | 6/2005 | Berthon-Jones |
| 6,910,481 B2 | 6/2005 | Kimmel et al. |
| 6,920,875 B1 | 7/2005 | Hill et al. |
| 6,920,877 B2 | 7/2005 | Remmers et al. |
| 6,932,084 B2 | 8/2005 | Estes et al. |
| 6,945,248 B2 | 9/2005 | Berthon-Jones |
| 6,948,497 B2 | 9/2005 | Zdrojkowski et al. |
| 6,960,854 B2 | 11/2005 | Nadjafizadeh et al. |
| 6,962,155 B1 | 11/2005 | Sinderby |
| 6,986,347 B2 | 1/2006 | Hickle |
| 7,000,612 B2 | 2/2006 | Jufari et al. |
| 7,013,892 B2 | 3/2006 | Estes et al. |
| 7,036,504 B2 | 5/2006 | Wallace et al. |
| 7,055,522 B2 | 6/2006 | Berthon-Jones |
| 7,073,501 B2 | 7/2006 | Remmers et al. |
| 7,077,131 B2 | 7/2006 | Hansen |
| RE39,225 E | 8/2006 | Isaza et al. |
| 7,100,607 B2 | 9/2006 | Zdrojkowski et al. |
| 7,100,608 B2 | 9/2006 | Brewer et al. |
| 7,117,438 B2 | 10/2006 | Wallace et al. |
| 7,137,389 B2 | 11/2006 | Berthon-Jones |
| 7,168,429 B2 | 1/2007 | Matthews et al. |
| 7,270,126 B2 | 9/2007 | Wallace et al. |
| 7,296,573 B2 | 11/2007 | Estes et al. |
| 7,367,337 B2 | 5/2008 | Berthon-Jones et al. |
| 7,369,757 B2 | 5/2008 | Farbarik |
| 7,370,650 B2 | 5/2008 | Nadjafizadeh et al. |
| 7,428,902 B2 | 9/2008 | Du et al. |
| 7,460,959 B2 | 12/2008 | Jafari |
| 7,475,685 B2 | 1/2009 | Dietz et al. |
| 7,487,773 B2 | 2/2009 | Li |
| 7,654,802 B2 | 2/2010 | Crawford, Jr. et al. |
| 7,661,428 B2 | 2/2010 | Berthon-Jones |
| 7,694,677 B2 | 4/2010 | Tang |
| 7,717,113 B2 | 5/2010 | Andrieux |
| D618,356 S | 6/2010 | Ross |
| 7,784,461 B2 | 8/2010 | Figueiredo et al. |
| 7,823,588 B2 | 11/2010 | Hansen |
| 7,855,716 B2 | 12/2010 | McCreary et al. |
| D632,796 S | 2/2011 | Ross et al. |
| D632,797 S | 2/2011 | Ross et al. |
| 7,891,354 B2 | 2/2011 | Farbarik |
| 7,893,560 B2 | 2/2011 | Carter |
| D638,852 S | 5/2011 | Skidmore et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 8,001,967 B2 | 8/2011 | Wallace et al. |
| D645,158 S | 9/2011 | Sanchez et al. |
| 8,021,310 B2 | 9/2011 | Sanborn et al. |
| D649,157 S | 11/2011 | Skidmore et al. |
| D652,521 S | 1/2012 | Ross et al. |
| D652,936 S | 1/2012 | Ross et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| D656,237 S | 3/2012 | Sanchez et al. |
| 8,181,648 B2 | 5/2012 | Perine et al. |
| 8,210,173 B2 | 7/2012 | Vandine |
| 8,210,174 B2 | 7/2012 | Farbarik |
| 8,220,456 B2 | 7/2012 | Kane et al. |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 8,457,706 B2 | 6/2013 | Baker, Jr. |
| 8,707,952 B2 * | 4/2014 | Jourdain ............ A61M 16/026 128/204.23 |
| 8,792,949 B2 | 7/2014 | Baker, Jr. |
| 8,939,150 B2 * | 1/2015 | Jourdain ............ A61M 16/026 128/204.23 |
| 9,254,369 B2 * | 2/2016 | Jourdain ............ A61M 16/026 |
| 2004/0163648 A1 | 8/2004 | Burton |
| 2004/0187870 A1 | 9/2004 | Matthews et al. |
| 2005/0039748 A1 | 2/2005 | Andrieux |
| 2005/0139212 A1 | 6/2005 | Bourdon |
| 2005/0188991 A1 | 9/2005 | Sun et al. |
| 2005/0241639 A1 | 11/2005 | Zilberg |
| 2006/0000475 A1 | 1/2006 | Matthews et al. |
| 2006/0011200 A1 | 1/2006 | Remmers et al. |
| 2006/0086357 A1 | 4/2006 | Soliman et al. |
| 2006/0102180 A1 | 5/2006 | Berthon-Jones |
| 2006/0118112 A1 | 6/2006 | Cattano et al. |
| 2006/0150974 A1 | 7/2006 | Berthon-Jones |
| 2006/0174883 A1 | 8/2006 | Aylsworth et al. |
| 2006/0201505 A1 | 9/2006 | Remmers et al. |
| 2006/0249156 A1 | 11/2006 | Moretti |
| 2006/0254588 A1 | 11/2006 | Brewer et al. |
| 2006/0272642 A1 | 12/2006 | Chalvignac |
| 2007/0017515 A1 | 1/2007 | Wallace et al. |
| 2007/0044796 A1 | 3/2007 | Zdrojkowski et al. |
| 2007/0077200 A1 | 4/2007 | Baker |
| 2007/0089738 A1 | 4/2007 | Soliman et al. |
| 2007/0101992 A1 | 5/2007 | Soliman et al. |
| 2007/0144522 A1 | 6/2007 | Eger et al. |
| 2007/0215146 A1 | 9/2007 | Douglas et al. |
| 2007/0221224 A1 | 9/2007 | Pittman et al. |
| 2007/0227537 A1 | 10/2007 | Bemister et al. |
| 2007/0272241 A1 | 11/2007 | Sanborn et al. |
| 2007/0284361 A1 | 12/2007 | Nadjafizadeh et al. |
| 2008/0000478 A1 | 1/2008 | Matthiessen et al. |
| 2008/0041382 A1 | 2/2008 | Matthews et al. |
| 2008/0041383 A1 | 2/2008 | Matthews et al. |
| 2008/0053441 A1 | 3/2008 | Gottlib et al. |
| 2008/0053442 A1 | 3/2008 | Estes et al. |
| 2008/0053443 A1 | 3/2008 | Estes et al. |
| 2008/0053444 A1 | 3/2008 | Estes et al. |

(56) References Cited

U.S. PATENT DOCUMENTS

| | | |
|---|---|---|
| 2008/0066753 A1 | 3/2008 | Martin et al. |
| 2008/0072896 A1 | 3/2008 | Setzer et al. |
| 2008/0072902 A1 | 3/2008 | Setzer et al. |
| 2008/0078390 A1 | 4/2008 | Milne et al. |
| 2008/0083644 A1 | 4/2008 | Janbakhsh et al. |
| 2008/0092894 A1 | 4/2008 | Nicolazzi et al. |
| 2008/0097234 A1 | 4/2008 | Nicolazzi et al. |
| 2008/0185002 A1 | 8/2008 | Berthon-Jones et al. |
| 2009/0165795 A1 | 7/2009 | Nadjafizadeh et al. |
| 2009/0171176 A1 | 7/2009 | Andersohn |
| 2009/0205661 A1 | 8/2009 | Stephenson et al. |
| 2009/0205663 A1 | 8/2009 | Vandine et al. |
| 2009/0241951 A1 | 10/2009 | Jafari et al. |
| 2009/0241952 A1 | 10/2009 | Nicolazzi et al. |
| 2009/0241953 A1 | 10/2009 | Vandine et al. |
| 2009/0241955 A1 | 10/2009 | Jafari et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0247837 A1 | 10/2009 | Ochs et al. |
| 2009/0247849 A1 | 10/2009 | McCutcheon et al. |
| 2009/0247853 A1 | 10/2009 | Debreczeny |
| 2009/0247891 A1 | 10/2009 | Wood |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2010/0011307 A1 | 1/2010 | Desfossez et al. |
| 2010/0024820 A1 | 2/2010 | Bourdon |
| 2010/0051026 A1 | 3/2010 | Graboi |
| 2010/0051029 A1 | 3/2010 | Jafari et al. |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0139660 A1 | 6/2010 | Adahan |
| 2010/0147303 A1 | 6/2010 | Jafari et al. |
| 2010/0186744 A1 | 7/2010 | Andrieux |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0236555 A1 | 9/2010 | Jafari et al. |
| 2010/0242961 A1 | 9/2010 | Mougel et al. |
| 2010/0249549 A1 | 9/2010 | Baker, Jr. et al. |
| 2010/0282259 A1 | 11/2010 | Figueiredo et al. |
| 2010/0288283 A1 | 11/2010 | Campbell et al. |
| 2010/0300446 A1 | 12/2010 | Nicolazzi et al. |
| 2011/0011400 A1 | 1/2011 | Gentner et al. |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0041849 A1 | 2/2011 | Chen et al. |
| 2011/0041850 A1 | 2/2011 | Vandine et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0175728 A1 | 7/2011 | Baker, Jr. |
| 2011/0196251 A1 | 8/2011 | Jourdain et al. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0230780 A1 | 9/2011 | Sanborn et al. |
| 2011/0249006 A1 | 10/2011 | Wallace et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0029317 A1 | 2/2012 | Doyle et al. |
| 2012/0030611 A1 | 2/2012 | Skidmore |
| 2012/0060841 A1 | 3/2012 | Crawford, Jr. et al. |
| 2012/0071729 A1 | 3/2012 | Doyle et al. |
| 2012/0090611 A1 | 4/2012 | Graboi et al. |
| 2012/0096381 A1 | 4/2012 | Milne et al. |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0137250 A1 | 5/2012 | Milne et al. |
| 2012/0167885 A1 | 7/2012 | Masic et al. |
| 2012/0185792 A1 | 7/2012 | Kimm et al. |
| 2012/0197578 A1 | 8/2012 | Vig et al. |
| 2012/0197580 A1 | 8/2012 | Vij et al. |
| 2012/0211008 A1 | 8/2012 | Perine et al. |
| 2012/0216809 A1 | 8/2012 | Milne et al. |
| 2012/0216810 A1 | 8/2012 | Jafari et al. |
| 2012/0216811 A1 | 8/2012 | Kimm et al. |
| 2012/0226444 A1 | 9/2012 | Milne et al. |
| 2012/0247471 A1 | 10/2012 | Masic et al. |
| 2012/0272960 A1 | 11/2012 | Milne |
| 2012/0272961 A1 | 11/2012 | Masic et al. |
| 2012/0272962 A1 | 11/2012 | Doyle et al. |
| 2012/0277616 A1 | 11/2012 | Sanborn et al. |
| 2012/0279501 A1 | 11/2012 | Wallace et al. |
| 2012/0304995 A1 | 12/2012 | Kauc |
| 2012/0304997 A1 | 12/2012 | Jafari et al. |
| 2013/0000644 A1 | 1/2013 | Thiessen |
| 2013/0006133 A1 | 1/2013 | Doyle et al. |
| 2013/0006134 A1 | 1/2013 | Doyle et al. |
| 2013/0008443 A1 | 1/2013 | Thiessen |
| 2013/0025596 A1 | 1/2013 | Jafari et al. |
| 2013/0025597 A1 | 1/2013 | Doyle et al. |
| 2013/0032151 A1 | 2/2013 | Adahan |
| 2013/0047989 A1 | 2/2013 | Vandine et al. |
| 2013/0053717 A1 | 2/2013 | Vandine et al. |
| 2013/0074844 A1 | 3/2013 | Kimm et al. |
| 2013/0081536 A1 | 4/2013 | Crawford, Jr. et al. |
| 2013/0104896 A1 | 5/2013 | Kimm et al. |
| 2013/0146055 A1 | 6/2013 | Jafari et al. |
| 2013/0167842 A1 | 7/2013 | Jafari et al. |
| 2013/0167843 A1 | 7/2013 | Kimm et al. |
| 2013/0192599 A1 | 8/2013 | Nakai et al. |
| 2013/0220324 A1 | 8/2013 | Jafari et al. |
| 2013/0255682 A1 | 10/2013 | Jafari et al. |
| 2013/0255685 A1 | 10/2013 | Jafari et al. |
| 2013/0284172 A1 | 10/2013 | Doyle et al. |
| 2013/0284177 A1 | 10/2013 | Li et al. |
| 2014/0000606 A1 | 1/2014 | Doyle et al. |

(56) References Cited

U.S. PATENT DOCUMENTS

| | | |
|---|---|---|
| 2014/0012150 A1 | 1/2014 | Milne et al. |
| 2014/0034054 A1 | 2/2014 | Angelico et al. |
| 2014/0041656 A1 | 2/2014 | Jourdain et al. |

FOREIGN PATENT DOCUMENTS

| | | |
|---|---|---|
| EP | 1270036 A2 | 1/2003 |
| WO | WO 2003/055552 A1 | 7/2003 |
| WO | WO 2005/105189 A1 | 11/2005 |
| WO | WO 2006/137784 A1 | 12/2006 |
| WO | WO 2009/123981 A1 | 10/2009 |

OTHER PUBLICATIONS

7200 Ventilatory System: Addendum/Errata. Nellcor Puritan Bennett, Part No. 4-023576-00, Rev. A, Apr. 1998, pp. 1-32.

800 Operator's and Technical Reference Manual. Series Ventilator System, Nellcor Puritan Bennett, Part No. 4-070088-00, Rev. L, Aug. 2010, pp. 1-476.

840 Operator's and Technical Reference Manual. Ventilator System, Nellcor Puritan Bennett, Part No. 4-075609-00, Rev. G, Oct. 2006, pp. 1-424.

PCT International Search Report and Written Opinion in Application PCT/US2011/023982, dated May 12, 2011, 15 pgs.

U.S. Appl. No. 12/769,876, Office Action dated Dec. 31, 2012, 6 pgs.

U.S. Appl. No. 12/769,876, Notice of Allowance dated May 13, 2013, 6 pgs.

U.S. Appl. No. 12/769,876, Notice of Allowance dated Aug. 22, 2013, 6 pgs.

U.S. Appl. No. 12/769,876, Notice of Allowance dated Nov. 14, 2013, 7 pgs.

U.S. Appl. No. 12/769,876, Notice of Allowance dated Dec. 13, 2013, 7 pgs.

U.S. Appl. No. 14/059,193, Office Action dated Aug. 12, 2014, 5 pgs.

U.S. Appl. No. 14/059,193, Notice of Allowance dated Sep. 22, 2014, 6 pgs.

U.S. Appl. No. 14/059,193, Amendment after Allowance filed Nov. 6, 2014, 3 pgs.

U.S. Appl. No. 14/570,106, Office Action dated Jul. 7, 2015, 5 pgs.

U.S. Appl. No. 14/570,106, Notice of Allowance dated Sep. 28, 2015, 5 pgs.

European Search Report in Application 17198666.4, dated May 4, 2018, 11 pages.

\* cited by examiner

LEAK DETERMINATION IN A BREATHING ASSISTANCE SYSTEM

CROSS-REFERENCE TO RELATED APPLICATIONS

This application is a continuation application of U.S. patent application Ser. No. 14/570,106 (now U.S. Pat. No. 9,254,369), entitled "LEAK DETERMINATION IN A BREATHING ASSISTANCE SYSTEM," filed on Dec. 15, 2014, which application is a continuation application of U.S. patent application Ser. No. 14/059,193 (now U.S. Pat. No. 8,939,150), filed on Oct. 21, 2013, which application is a continuation application of U.S. patent application Ser. No. 12/769,876 (now U.S. Pat. No. 8,707,952), filed Apr. 29, 2010, which application claims the benefit of U.S. Provisional Application No. 61/303,093, filed Feb. 10, 2010, the complete disclosures of which are hereby incorporated herein by reference.

TECHNICAL FIELD

The present disclosure relates generally to the field of breathing assistance systems, e.g., systems and methods for estimating leak flow in a breathing assistance system (e.g., a ventilator).

BACKGROUND

The present description pertains to breathing assistance devices, such as ventilators, for example. Modern ventilators commonly employ positive pressure to assist patient ventilation. For example, after determining a patient-initiated or timed trigger, the ventilator delivers a specified gas mixture into an inhalation airway connected to the patient to track a specified desired pressure or flow trajectory, causing or assisting the patient's lungs to fill. Upon reaching the end of the inspiration, the added support is removed and the patient is allowed to passively exhale and the ventilator controls the gas flow through the system to maintain a designated airway pressure level (PEEP) during the exhalation phase. Other types of ventilators are non-triggered, and mandate a specified breathing pattern regardless of patient effort.

Modern ventilators typically include microprocessors or other controllers that employ various control schemes. These control schemes are used to command a pneumatic system (e.g., valves) that regulates the flow rates of breathing gases to and/or from the patient. Closed-loop control is often employed, using data from pressure, flow, and/or other types of sensors.

Certain ventilation configurations provide the potential for leaks occurring at various locations in the ventilation system, e.g., at connection interfaces between system components or at the interface between a breathing mask or tube and the patient's mouth or face. The magnitude of leaks in the system can vary from setting to setting, and/or dynamically within a particular setting, dependent upon a host of variables, Leaks can impair triggering (transition into inhalation phase) and cycling (transition into exhalation phase) of the ventilator, and thus cause problems with patient-device synchrony, undesirably increase patient breathing work, degrade advisory information available to treatment providers, and/or otherwise compromise the desired respiratory therapy.

Figure 1A:
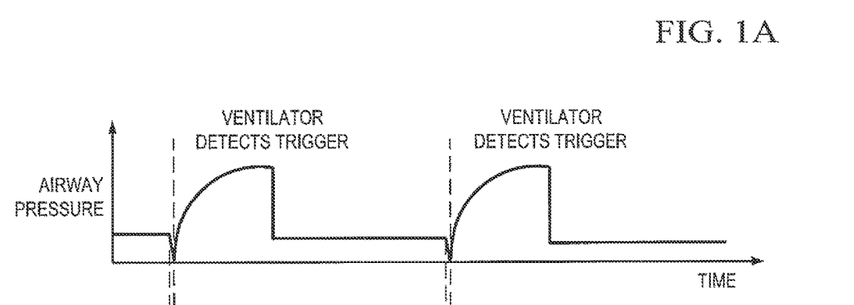
FIGS. 1A and 1B show example pressure and flow waveforms, respectively, to illustrate certain effects commonly caused by leaks in a breathing assistance system, such as a ventilator.
Figure 1B:
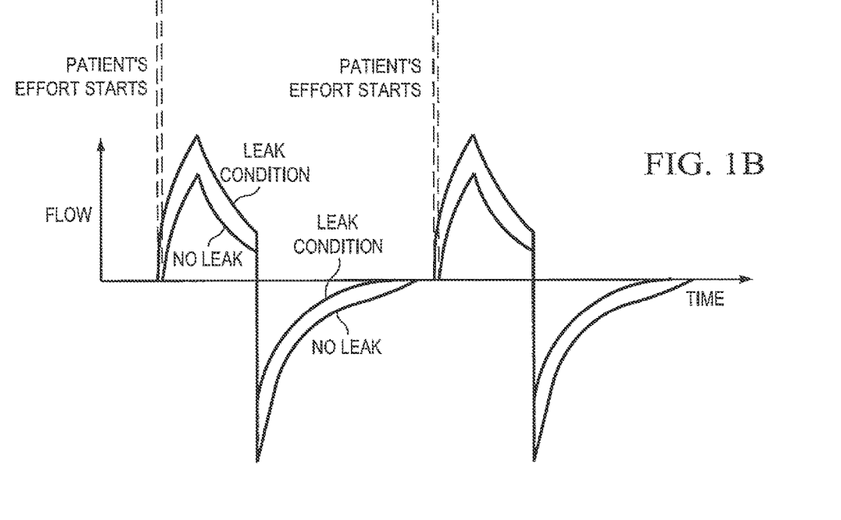

FIGS. 1A and 1B provide an example pressure waveform and corresponding flow waveform to illustrate one effect of system leaks. FIG. 3A illustrates an example desired pressure waveform in a "Pressure Support" ventilation mode. FIG. 3B illustrates two different flow waveforms that provide the desired pressure waveform: one waveform in a configuration with no leaks, and one waveform in a configuration with leaks. As shown, during inspiration more flow is required in the leak configuration to achieve the same pressure level as compared to no-leak configuration. Further, during exhalation, a portion of the volume exhaled by the patient may exit through the leak and be missed by the ventilator exhalation flow measurement subsystem. In many cases, the goal of the control system is to deliver a controlled pressure or flow profile or trajectory (e.g., pressure or flow as a function of time) during the inspiratory phase of the breathing cycle. In other words, control is performed to achieve a desired time-varying pressure or flow output from a pneumatic system, with an eye toward causing or aiding the desired tidal breathing (e.g., the desired pressure profile shown in FIG. 3A).

Improper leak accounting can compromise the timing and magnitude of the control signals applied to the pneumatic system, especially during volume delivery. Also, inaccurate (or inadequate) leak compensation can jeopardize spirometry and patient data monitoring and reporting calculations. For example, the pressure applied from the pneumatic system to the patient may cause leakage of breathing gas to atmosphere. This leakage to atmosphere may occur, for example, at some point on the inspiratory limb or expiratory limb of the patient circuit, or at the connection between the breathing circuit and pneumatic system or between the breathing circuit and the patient interface (e.g., facial mask or endotracheal tube).

In the case of non-invasive ventilation, it is typical for some amount of breathing gas to escape via the opening defined between the patient interface (e.g., facial mask) and the surface of the patient's face. In facial masks, this opening can occur at a variety of locations around the edge of the mask, and the size and deformability of the mask can create significant leak variations. Due to the elastic nature of these masks and the movement of the patient, a leak compensation strategy assuming a constant size leak orifice (and thus constant leak flow) may be inadequate.

Accurately estimating and/or accounting for the magnitude of the leak flow may provide significant advantages. In order for a controller to command the pneumatic system to deliver the desired amount of volume/pressure to the patient at the desired time and measure/estimate the accurate amount of gas volume exhaled by the patient, the controller needs knowledge of the extent of the leak flow over time. The fact that the leak magnitude changes dynamically during operation of the ventilator introduces additional complexity to the problem of leak modeling.

Triggering and cycling (patient-ventilator) synchrony may also be compromised by sub-optimal leak estimation. In devices with patient-triggered and patient-cycled modalities that support spontaneous breathing efforts by the patient, it can be important to accurately detect when the patient wishes to inhale and exhale. Detection commonly occurs by using accurate pressure and/or lung flow (flow rates into or out of the patient's lung) variations. Leaks in the airway may cause an error in the signals to the sensors of the pneumatic system. This error may impede the ability of ventilator to detect the start of an inspiratory effort, which in turn compromises the ability of the controller to drive the pneumatic system in a fashion that is synchronous with the patient's spontaneous breathing cycles.

Accordingly, attempts have been made in existing control systems compensate for ventilation system leaks, which first involves estimation of the leak. However, prior techniques for determining leaks have had limited success, particularly in the case of patient-triggered breathing (i.e., patient-triggered inspiration).

SUMMARY

In some embodiments, a method for estimating a leak flow in a breathing assistance system including a ventilation device connected to a patient is provided. The method may include accessing data of a flow waveform indicating the flow of gas between the ventilation device and the patient, identifying a specific portion of the flow waveform, and performing a linear regression of the identified portion of the flow waveform to determine an estimated leak flow in the breathing assistance system.

In some embodiments, a method for controlling breathing assistance provided to a patient includes providing breathing assistance to a patient according to one or more operational parameters, estimating a leak flow, and controlling at least one of the operational parameters based at least on the estimated leak flow. Estimating the leak flow includes accessing data of a flow waveform indicating the flow of gas between the ventilation device and the patient, identifying a specific portion of the flow waveform, and performing a linear regression of the identified portion of the flow waveform to determine an estimated leak flow in the breathing assistance system.

In some embodiments, a breathing assistance system for providing breathing assistance to a patient includes a pneumatic system for providing breathing assistance to a patient, and a controller configured to control one or more operational parameters of the pneumatic system. The controller is configured to estimate a leak flow in a breathing assistance system including a ventilation device connected to a patient by accessing data of a flow waveform indicating the flow of gas between the ventilation device and the patient, identifying a specific portion of the flow waveform, and performing a linear regression of the identified portion of the flow waveform to determine an estimated leak flow in the breathing assistance system.

In some embodiments, a controller for a breathing assistance system includes logic instructions embodied in tangible computer readable media and executable by one or more processors. The logic instructions are executable to access data of a flow waveform indicating the flow of gas between the ventilation device and the patient, identify a specific portion of the flow waveform, and perform a linear regression of the identified portion of the flow waveform to determine an estimated leak flow in the breathing assistance system.

DETAILED DESCRIPTION OF THE DRAWINGS

As described below, a ventilation system may be provided with control schemes that provide improved leak estimation and/or compensation. In general, these control schemes estimate the system leak based on a linear regression of flow during an end portion of the exhalation phase (referred to herein as the "end exhalation steady phase"). The present discussion focuses on specific example embodiments, though it should be appreciated that the present systems and methods are applicable to a wide variety of ventilator and other breathing assistance systems.

Figure 2:
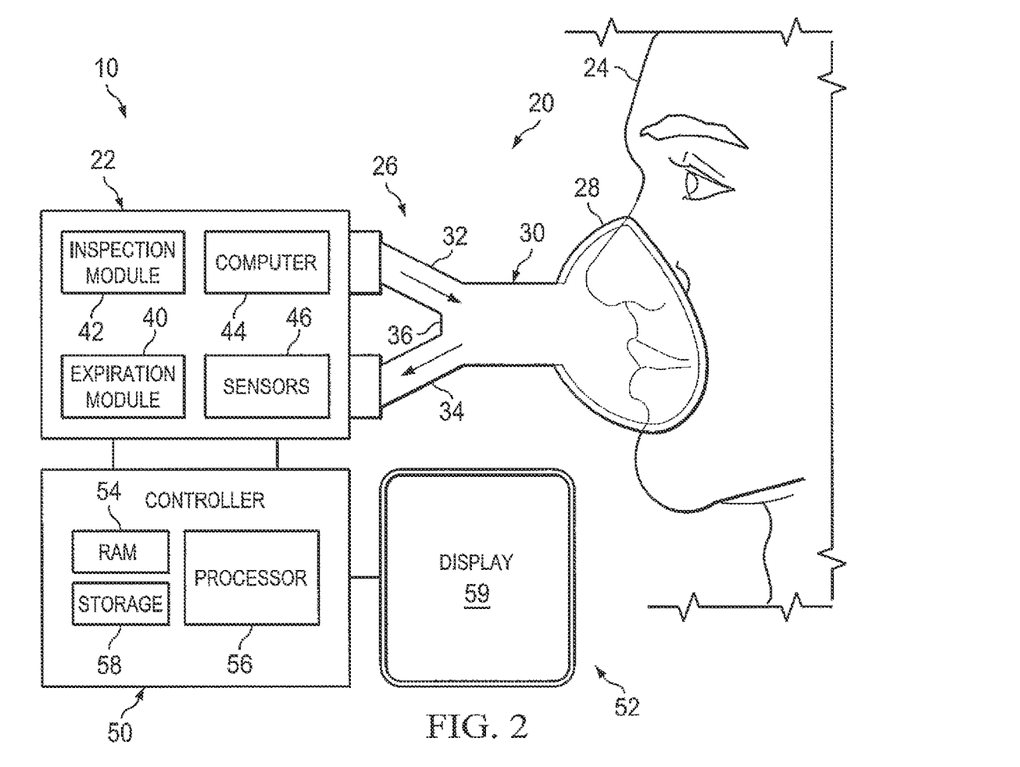
FIG. 2 illustrates an example ventilation system including a controller for estimating system leaks, according to certain embodiments.

FIG. 2 illustrates an example breathing assistance system 10 according to certain embodiments of the present disclosure. Breathing assistance system 10 includes a ventilator 20 connected to a patient 24 by an airway 26. Ventilator 20 includes a pneumatic system 22, a controller 50, and a display 59. Pneumatic system 22 circulates breathing gases to and/or from patient 24 via airway 26, which couples patient 24 to pneumatic system 22 via physical patient interface 28 and breathing circuit 30. Breathing circuit 30 may include any conduits for communicating gas to and/or from patient 24, e.g., a two-limb or one-limb circuit for carrying gas to and/or from patient 24. A wye fitting 36 may be provided as shown to couple patient 24 interface to breathing circuit 30.

As used herein, the term "gas" may refer to any one or more gases and/or vaporized substances suitable to be delivered to and/or from a patient via one or more breathing orifices (e.g., the nose and/or mouth), such as air, nitrogen, oxygen, any other component of air, vaporized water, vaporized medicines, and/or any combination of two or more of the above, $CO_2$, for example. As used herein, the term "patient" may refer to any person or animal that may receive breathing assistance from system 10, regardless of the medical status, official patient status, physical location, or any other characteristic of the person. Thus, for example, patients may include persons under official medical care (e.g., hospital patients), persons not under official medical care, persons receiving care at a medical care facility, persons receiving home care, etc.

The present systems and methods have proved particularly advantageous in non-invasive settings, such as with facial breathing masks, as those settings typically are more susceptible to leaks. However, leaks do occur in a variety of settings, and the present description contemplates that patient interface 28 may be invasive or non-invasive, and of any configuration suitable for communicating a flow of breathing gas from patient circuit 30 to an airway of patient 24. Examples of such patient interfaces 28 include nasal masks, nasal/oral masks (e.g., as shown in FIG. 2), full-face masks, nasal prongs, tracheal tubes, endotracheal tubes, nasal pillows, etc.

Pneumatic system 22 may be configured in a variety of ways. In the illustrated example, system 22 includes an expiratory module 40 coupled with an expiratory limb 34 and an inspiratory module 42 coupled with an inspiratory limb 32. A gas flow source 44 (e.g., a compressor, one or more tanks of compressed gas, a wall outlet through which pressurized air may be supplied (e.g., in a hospital or clinic), etc.) is coupled with inspiratory module 42 to provide a gas source for ventilatory support via inspiratory limb 32. Pneumatic system 22 also includes one or more sensors 46 for measuring various parameters such as pressure, flow, temperature, etc. Although sensors 46 are illustrated as being located within pneumatic system 22, sensors 46 may be located at any suitable location or locations in breathing assistance system 10, e.g., within a housing of pneumatic system 22, along breathing circuit 30, coupled to patient interface 28, etc. Pneumatic system 22 may also include a variety of other components, e.g., sources for pressurized air and/or oxygen, mixing modules, valves, tubing, accumulators, filters, etc.

Controller 50 is operatively coupled to pneumatic system 22 and an operator interface 52 enabling an operator (e.g., a physician) to interact with ventilator 20 (e.g., to change ventilator settings, select operational modes, view monitored parameters, etc.). Controller 50 may include memory 54 (e.g., RAM or any other suitable volatile and/or nonvolatile memories), one or more processors 56, data storage 58, and/or other components of the type commonly found in command and control computing devices. As described in more detail below, controller 50 issues commands to pneumatic system 22 in order to control the breathing assistance provided to patient 24 by ventilator 20. The specific commands may be based on inputs received from patient 24, pneumatic system 22 (e.g., pressure and/or flow sensors 46), operator interface 52, and/or other components of breathing assistance system 10. In the illustrated example, operator interface 52 includes a display device 59. In some embodiments, display device 59 includes a touch-sensitive interface or other input devices, enabling display device 59 to serve both as an input and output device.

Figure 3:
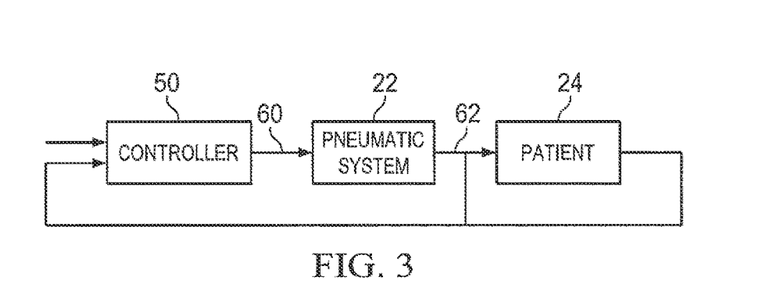
FIG. 3 illustrates an example control system and method that may be employed in the ventilation system of FIG. 2, according to certain embodiments.

FIG. 3 illustrates an example control system and method that may be employed in ventilation system 10 of FIG. 2, according to certain embodiments. As shown, controller 50 issues control commands 60 to drive pneumatic system 22 and thereby circulate breathing gas to and/or from patient 24. The illustrated interaction between pneumatic system 22 and patient 24 may be viewed in terms of pressure and/or flow "signals." For example, signal 62 may be an increased pressure which is applied to patient 24 via inspiratory limb 32. Control commands 60 are based upon inputs received at controller 50 which may include, among other things, inputs from operator interface 52, and feedback from pneumatic system 22 (e.g., from pressure and/or flow sensors 46) and/or sensed from patient 24.

In many cases, it may be desirable to establish a baseline pressure and/or flow trajectory for a given respiratory therapy session. The volume of breathing gas delivered to the patient's lungs and the volume of the gas exhaled by the patient are measured or determined, and the system leak is estimated are accounted for to ensure accurate ventilation support and data reporting and monitoring. Accordingly, the more accurate the leak estimation, the better the baseline calculation of delivered and exhaled gas volume, as well as event detection (e.g., triggering and phase transitions).

In some embodiments, controller 50 may calculate a "leak factor" K that may be used by controller 50 for compensating for system leaks and/or for other functionality. The leak factor K may be estimated by Equation (1):

$$K = Q\text{leak}^2/\text{PEEP} \tag{1}$$

where:
Qleak=estimated flow at the end of exhalation obtained by linear regression interpolation over an "end exhalation steady phase" ("EESP phase"), and
PEEP=Patient pressure over the exhalation steady phase. PEEP may be determined using any known techniques. For example, PEEP for each breath may be calculated by an averaging of patient pressure measurements over the EESP phase for that breath. Alternatively, PEEP could be estimated using a linear regression technique similar to the techniques disclosed herein for estimating leak flow (Qleak).

Thus, the estimation of leak flow (Qleak) may be achieved by a technique including a linear regression of measured exhalation flow during a determined end portion of the exhalation phase, referred to herein as the "end exhalation steady phase" (or "EESP phase"), In general, the leak flow estimation technique includes identifying the end of the exhalation phase of a breath cycle (i.e., the beginning of the subsequent inhalation phase), analyzing the exhalation flow waveform during the exhalation phase to determine an "end exhalation steady phase" ("EESP phase"), performing a linear regression on the determined EESP phase to calculate an estimated end-of-exhalation leak flow at exhalation pressure, calculating a leak factor based on the estimated leak flow, and using the calculated leak factor to compensate for the leak and/or for other functionality. The leak flow estimation technique is discussed in greater detail below, with reference to FIG. 4.

Figure 4:
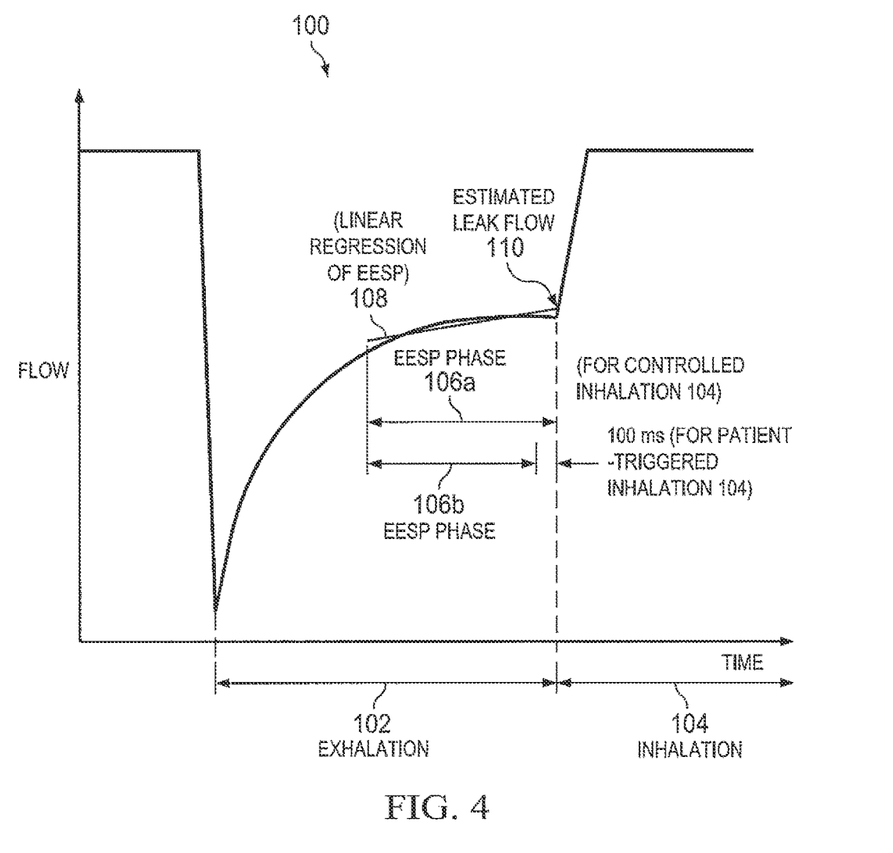
FIG. 4 illustrates an example flow waveform along with graphics illustrating certain techniques for estimating system leaks, according to certain embodiments.

FIG. 4 illustrates an example flow waveform 100 (i.e., flow vs. time) for an exhalation phase 102 of a breath cycle, followed by the beginning of the inspiratory phase 104 for the next breath cycle, for graphically illustrating the technique for calculating the estimated leak flow according to the technique proved herein. As discussed above, the technique includes identifying the end of exhalation phase 102 (i.e., the beginning of inhalation phase 104), analyzing the flow waveform during exhalation phase 102 to determine an "end exhalation steady phase" ("EESP phase") 106, performing a linear regression (indicated by line 108) on the determined EESP phase 106 to calculate an estimated end-of-exhalation leak flow 110. The leak flow 110 may then be used to calculate a leak factor, which may then be used by controller 50 for compensating for the leak and/or for other functions of ventilator 20.

In some embodiments, the beginning and/or end of EESP phase 106 depends on Whether the next breath (which includes inhalation phase 104) is a controlled breath or a patient-triggered breath. Thus, as shown in FIG. 4, EESP phase 106a refers to an EESP phase when the next breath is a controlled breath, and EESP phase 106b refers to an EESP phase when the next breath is a patient-triggered breath.

The technique operates according to a set of rules, executed by controller 50, for determining the beginning and the end of EESP phase 106a/106b. In certain embodiments, the rules specify:

If the Next Breath a Controlled Breath:
1. The beginning of exhalation phase 102 is determined in any suitable manner, e.g., by the I/E ratio and R-Rate (implying a fixed inspiratory time) in a PRESS A/C mode or based on the "E Sens" setting in PSV mode.

2A. The end of exhalation phase 102 is defined by the breath rate ("R-Rate") set in controller 50 (e.g., automatically set based on the current ventilation mode, or manually set by the physician).

3A. The end of EESP phase 106 is defined as the end of exhalation phase 102

4. The duration of EESP phase 106 is some multiple of 100 ms and cannot exceed 600 ms. Thus, EESP phase 106 is either 100, 200, 300, 400, 500, or 600 ms.

5. The duration of EESP phase 106 cannot exceed "exhalation duration/2". "Exhalation duration" is defined as the duration from the beginning of exhalation phase 102 (Rule 1) to the end of exhalation phase 102 (Rule 2A).

6. Subject to the limitations set forth in Rules 4 and 5, the duration of EESP phase 106 is determined by applying a "≤5% variance test" to successive 100 ms periods going backwards in time from the end of exhalation phase 102 (determined by Rule 2) to identify a string of zero, one, or more 100 ms periods that qualify as EESP phase 106. A particular 100 ms period qualifies for EESP phase 106 if the average flow rate varies by 5% from the average flow rate of the final 100 ms period of exhalation phase 102.

More specifically, the average flow rate of the 100 ms period that ends at the end of exhalation phase 102 (defined as $P_{final}$) is determined and defined as $AFR_{Pfinal}$. The average flow rate of each successive 100 ms period ($P_{final-1}$, $P_{final-2}$, ... $P_{final-5}$) going backwards from $P_{final}$ (defined as $AFR_{Pfinal-1}$, $AFR_{Pfinal-2}$, ... $AFR_{Pfinal-5}$) is determined and compared to $AFR_{Pfinal}$, until a 100 ms period ($P_{final-1}$, $P_{final-2}$, ... $P_{final-5}$) is identified for which the average flow rate ($AFR_{Pfinal-1}$, $AFR_{Pfinal-2}$, ... $AFR_{Pfinal-5}$) varies from $AFR_{Pfinal}$ by more than 5%. The duration of EESP phase 106 is defined as $P_{final}$ plus each previous 100 ms period ($P_{final-1}$, $P_{final-2}$, ... $P_{final-5}$) that meets the "≤5% variance test" (i.e., qualifying periods), but not the time period that failed the "≤5% variance test" (i.e., the non-qualifying period) and any previous time periods. If the average flow rate of the 100 ms period immediately preceding $P_{final}$ (i.e., $P_{final-1}$) fails the "≤5% variance test", then EESP phase 106 is defined as $P_{final}$.

As mentioned at the beginning of Rule 6, the duration of EESP phase 106 as determined by the "≤5% variance test" is subject to the limitations of Rules 4 and 5. Thus, where the "≤5% variance test." process described above would result in a EESP phase 106 duration that would exceed the limits prescribed by Rule 4 and/or 5, the EESP phase 106 duration is instead capped by the limits of Rule 4 and/or 5. The limits of Rules 4 and 5 may be applied during or after the "≤5% variance test" process described above, For example, in some embodiments, the process of Rule 6 may be completed and the resulting EESP phase 106 duration is limited by Rule 4 and/or 5, if applicable. In other embodiments, the process of Rule 6 terminates before testing any 100 ms period ($P_{final-1}$, $P_{final-2}$, ... $P_{final-5}$) that would, if found to be a qualifying period, exceed the limits of Rule 4 and/or 5.

If the Next Breath a Patient-Triggered Breath:

1. Same as Rule 1 above for the scenario of a subsequent controlled breath.

2B. The end of exhalation phase 102 is defined by the detection of an inspiratory trigger.

3B. The end of EESP phase 106 is defined as predetermined duration, 100 ms, before the end of exhalation phase 102.

4. Same as Rule 4 above for the scenario of a subsequent controlled breath.

5. Same as Rule 5 above for the scenario of a subsequent controlled breath.

6. Same as Rule 6 above for the scenario of a subsequent controlled breath.

In the example Rules presented above, only Rules 2 and 3 differ depending on whether the next breath is a patient-triggered breath. Thus, only Rules 2 and 3 are distinguished by 2A/2B and 3A/3B notations.

It should be understood that the various values set forth in the preceding Rules are examples only, and any other suitable values may be used. For example, the following values are examples only and any other suitable values may be used:

the 600 ms limit for EESP phase 106 set forth in Rule 4, the number of possible EESP phase 106 durations (6) set forth in Rule 4, the "exhalation duration/2" formula set forth in Rule 5, the 100 ms period duration set forth in Rules 3A/3B and 6, and the 5% variance threshold set forth in Rule 6, It should also be understood that depending on the particular embodiment, one, some, or all of the Rules set forth herein may be used. Further, any one or more additional Rules may be used in conjunction with any or all of the Rules set forth above.

After determining the beginning and the end (and thus the duration) of EESP phase 106a/106b, controller 50 may perform a linear regression interpolation of flow waveform 100 over the determined EESP phase 106a/106b, and determine Qleak as the leak flow at the end of exhalation phase 102 according to the linear regression interpolation. Controller 50 may use any known techniques for performing the linear regression analysis.

After determining the end of exhalation flow, Qleak, controller 50 may calculate the leak factor K using Equation (1) above. Controller 50 may then use the calculated leak factor K for compensating for the leak and/or for other functionality. The leak factor K may be used for various purposes. For example, controller 50 may use the leak factor K for evaluating the real patient flow (e.g., by subtracting the inspiration leak flow $Qleak'=(K*Pressure)^{0.5}=Qleak*(Pressure/PEEP)^{0.5}$ at the current pressure from the flow measured by flow sensor 46). Then controller 50 may calculate the tidal volume by integrating Qleak' over the inspiratory phase. As another example, Qleak' can also be used for determining the inspiration phase ending (e.g., using an Esens function based on a peak flow % threshold) that is corrupted by any leak occurring if no leak compensation is implemented. As another example, Qleak may be used to display a leak value on display 59 for the user to track the leak variations of the interface. In some embodiments, Qleak is used in pressure controlled/support breath. However, in other embodiments, Qleak may be used for driving directly an inspiratory flow in a volume controlled breath.

Any or all of Qleak, PEEP, and leak factor K may be recalculated/determined after each breath, at regular intervals (e.g., after every x breaths or after every y seconds), upon a predetermined triggering event (e.g.,) a patient-triggered breath, or a Change in Qleak or PEEP greater than a preset threshold value), or according to any other frequency or timing. In addition, any or all of Qleak, PEEP, and leak factor K may be utilized by controller 50 as individual calculated values, as average values of multiple iterations (e.g., a rolling average of the last five calculated Qleak values or K values), or according to any other suitable algorithm.

Any or all of the Rules, calculations, estimations, and other functions set forth herein may be implemented in any suitable hardware, software, firmware, or any combination thereof. For example, the Rules and equations set forth above may be embodied in firmware or software stored in memory or other computer readable medium associated with or accessible by controller 50.

Figure 5:
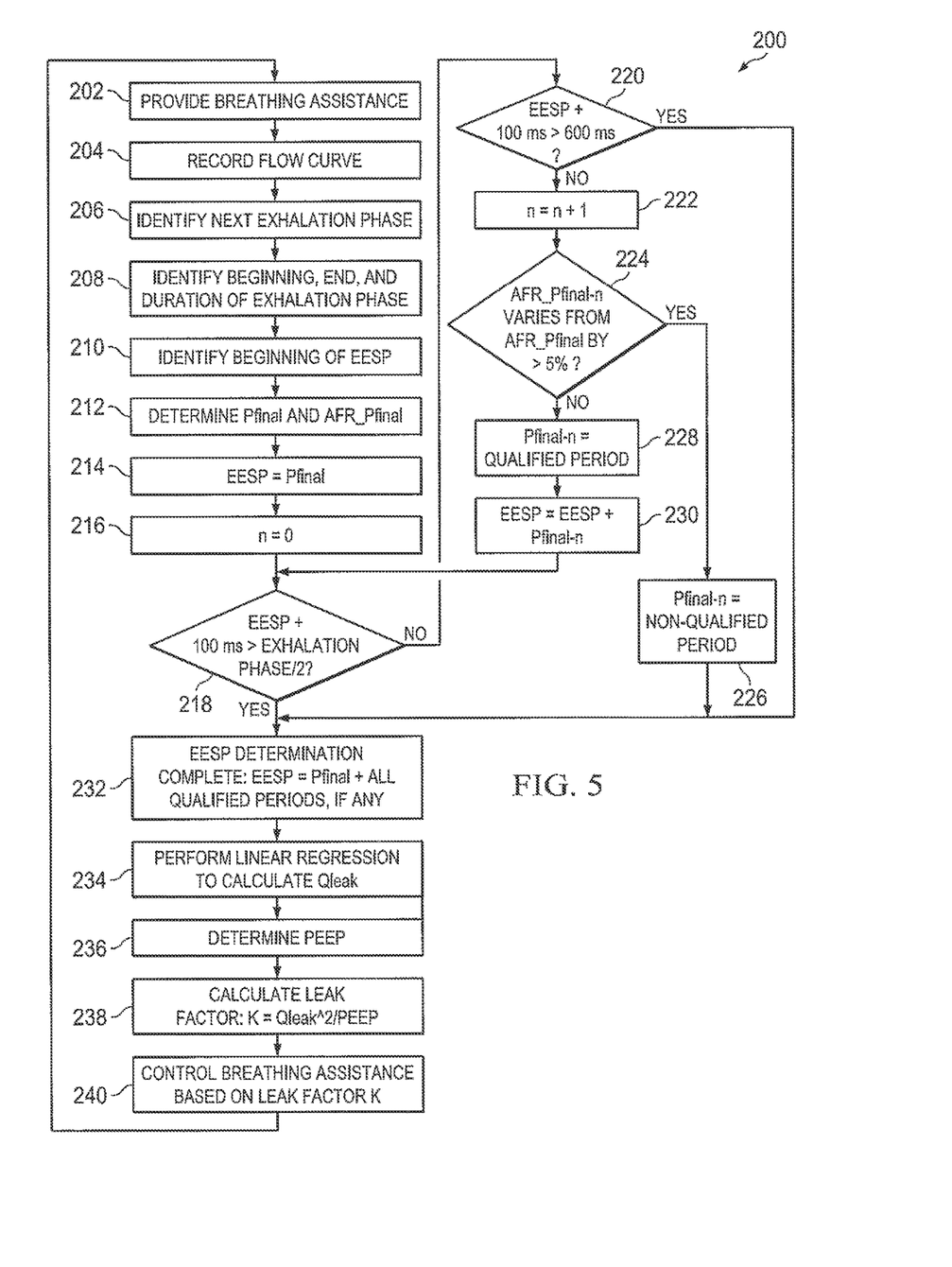
FIG. 5 illustrates an example method of estimating a leak flow in a ventilation system (e.g., the ventilation system of FIG. 2), according to certain embodiments.

FIG. 5 illustrates an example method 200 for determining a leak factor, and regulating one or more functions of ventilator 20 based on the determined leak factor, according to certain example embodiments. More specifically, method 200 incorporates the Rules and techniques discussed above, according to certain example embodiments.

At step 202, ventilator 20 provides breathing assistance to patient 24, e.g., as controlled by controller 50 based on the current ventilation mode and/or settings.

At step 204, controller 50 records a flow vs. time waveform, e.g., which may be similar to the waveform shown in FIG. 1B.

At step 206, controller 50 identifies the exhalation phase fur the next breath cycle.

At step 208, controller 50 identifies the beginning, end, and duration of the identified exhalation phase. Controller 50 may use any suitable techniques or rules for determining the beginning and end of the exhalation phase, e.g., example Rules 1 and 2A/2B presented above.

At steps 210-232, controller 50 analyzes the exhalation phase flow waveform to determine the "end exhalation steady phase" (EESP phase) for the exhalation phase.

At step 210, controller 50 identifies the end of the EESP phase. Controller 50 may use any suitable techniques or rules, e.g., example Rules 3A/3B presented above.

At step 212, controller 50 identifies the 100 ms period that ends at the end of the exhalation phase ($P_{final}$) and determines the average flow rate during $P_{final}$ ($AFR_{Pfinal}$).

At step 214, controller 50 includes $P_{final}$ in the EESP phase being determined.

At step 216, controller 50 resets a counter "n" equal to 0.

At step 218, controller 50 determines whether the EESP phase duration plus 100 ms is greater than one-half of the duration of the identified exhalation phase determined at step 208 (see Rule 5 above). If so, the EESP phase determination is complete, and the method skips to step 232. If not, the method proceeds to step 220.

At step 220, controller 50 determines whether the EESP phase duration plus 100 ms is greater than 600 ms (see Rule 4 above). If so, the EESP phase determination is complete, and the method skips to step 232. If not, the method proceeds to step 222.

At step 222, controller 50 increases the counter "n" to "n+1".

At step 224, controller 50 applies the "≤5% variance test" to the period $P_{final-n}$. Specifically, controller 50 determines whether the average flow rate during the period $P_{final-n}$ ($AFR_{Pfinal}$) varies from the average flow rate during the period $P_{final}$ ($AFR_{Pfinal}$) by more than 5%. If so, $P_{final-n}$ is identified as a Non-Qualified Period at step 226 and is not included from the EESP phase, the EESP phase determination is complete, and the method skips to step 232.

Alternatively, if $AFR_{Pfinal}$ varies from $AFR_{Pfinal}$ by less than or equal to 5%, $P_{final-n}$ is identified as a Qualified Period at step 228 and included in the EESP at step 230. The method then returns to step 218 to analyze the next previous 100 ms period. Steps 218-230 are repeated until a threshold is exceeded at steps 218 or 220 or until a Non-Qualified Period is identified at step 226, any of which occurrences completes the EESP determination at step 232.

As indicated as step 232, the final determined EESP for the exhalation phase being analyzed includes the final period $P_{final}$ and each Qualified Period determined at step 228, if any.

At step 234, controller 50 performs a linear regression of flow waveform 100 over the determined EESP phase, and determines leak flow, Qleak, at the end of exhalation phase 102, e.g., as shown in FIG. 4. Controller 50 may use any known techniques for performing the linear regression analysis.

At step 236, controller 50 calculates PEEP using any suitable technique, e.g., by averaging pressure over the EESP.

At step 238, controller 50 calculates a leak factor K using Equation (1) above, based on the Qleak and PEEP values determined at steps 234 and 236.

At step 240, controller 50 may then use the calculated leak factor K for controlling any one or more functions of ventilator 20, according to any predetermined rules or algorithms.

The method then returns to step 202 for continued ventilation assistance and analysis of the next exhalation phase.

The techniques discussed herein may provide one or more various advantages. For example, using the linear regression techniques discussed herein, variation associated with raw measurements regarding leak determination may be reduced. The techniques introduce a level of filtering but without the type/level of error associated with other filtering methods, such as averaging. As another example, the techniques discussed herein may be more robust to patient triggering than known techniques, in which patient triggering often negatively affects the accuracy of the leak determination.

It will be appreciated that while the disclosure is particularly described in the context of breathing assistance systems, the apparatuses, techniques, and methods disclosed herein may be similarly applied in other contexts. For example, similar principles may be applied in certain CPAP devices, BiPAP devices, or other suitable types of breathing assistance devices. Additionally, it should be understood that various changes, substitutions and alterations can be made herein without departing from the spirit and scope of the disclosure as illustrated by the following claims.

What is claimed is:

1. A breathing assistance system including a ventilation device for delivering respiratory gases to a patient, the breathing assistance system having a controller for estimating a leak flow by:

monitoring a flow of gas between the ventilation device and the patient, wherein the monitored flow of gas is represented by a flow waveform;

determining a first flow rate for a first period of the flow waveform;

determining a second flow rate for at least a second period of the flow waveform;

defining a steady phase portion of the flow waveform to include the first period and the second period when the second flow rate varies from the first flow rate by less than a predetermined amount;

determining an estimated leak flow based on the steady phase portion of the flow waveform; and in response to determining the estimated leak flow, controlling at least one of one or more operational parameters to target a positive end expiratory pressure (PEEP).

2. The breathing assistance system according to claim 1, further comprising:

in response to determining the estimated leak flow, controlling at least one of the one or more operational parameters to detect a triggering event.

3. The breathing assistance system according to claim 1, further comprising:

identifying a specific portion of the flow waveform comprising the first period and the second period by determining that a flow variation in the flow waveform falls within a predetermined variation threshold.

4. The breathing assistance system according to claim 1, further comprising:

determining a third representative flow rate for a third period of the flow waveform; and defining the steady phase portion to include the first period, the second period, and the third period when the third representative flow rate varies from the first representative flow rate by less than the predetermined amount.

5. The breathing assistance system according to claim 1, wherein the second period immediately precedes the first period.

6. The breathing assistance system according to claim 4, wherein the third period immediately precedes the second period, and wherein the second period immediately precedes the first period.

7. The breathing assistance system according to claim 1, further comprising:
determining a third representative flow rate for a third period of the flow waveform; and
defining the steady phase portion to include the first period and the second period when the third representative flow rate varies from the first representative flow rate by more than the predetermined amount.

8. The breathing assistance system according to claim 1, wherein the estimated leak flow is determined by performing an interpolation of the steady phase portion of the flow waveform.

9. The breathing assistance system according to claim 8, wherein the interpolation is linear regression.

10. A method for estimating a leak flow in a breathing assistance system including a ventilation device connected to a patient, the method comprising:
monitoring a flow of gas between the ventilation device and the patient, wherein the monitored flow of gas is represented by a flow waveform;
determining a first representative flow rate for a first period of the flow waveform;
determining a second representative flow rate for at least a second period of the flow waveform;
defining a steady phase portion of the flow waveform to include the first period and the second period when the second representative flow rate varies from the first representative flow rate by less than a predetermined amount;
determining an estimated leak flow based on the steady phase portion of the flow waveform; and
in response to determining the estimated leak flow, adjusting at least one operational parameter of the ventilation device to detect a triggering event.

11. The method according to claim 10, further comprising:
in response to determining the estimated leak flow, adjusting at least one operational parameter of the ventilation device to target a positive end expiratory pressure (PEEP).

12. The method according to claim 10, further comprising:
identifying a specific portion of the flow waveform comprising the first period and the second period by determining that the steady phase portion of the flow waveform has a flow variation within a predetermined variation threshold.

13. The method according to claim 10, further comprising:
determining a third representative flow rate for a third period of the flow waveform; and
defining the steady phase portion to include the first period and the second period when the third representative flow rate varies from the first representative flow rate by more than the predetermined amount.

14. The method according to claim 10, wherein the estimated leak flow is determined by performing an interpolation of the steady phase portion of the flow waveform.

15. The method according to claim 14, wherein the interpolation is linear regression.

16. A ventilation device comprising:
at least one processor; and
at least one memory storing computer-readable instructions that when executed by the at least one processor cause the ventilation device to:
monitor a flow of gas between the ventilation device and the patient, wherein the monitored flow of gas is represented by a flow waveform;
determine a first representative flow rate for a first period of the flow waveform;
determine a second representative flow rate for at least a second period of the flow waveform;
define a steady phase portion of the flow waveform to include the first period and the second period when the second representative flow rate varies from the first representative flow rate by less than a predetermined amount;
determine an estimated leak flow based on the steady phase portion of the flow waveform; and
control at least one operational parameter based on the estimated leak flow to deliver an adjusted pressure of gas to the patient.

17. The ventilation device according to claim 16, the computer-readable instructions further causing the ventilation device to:
determine a third representative flow rate for a third period of the flow waveform; and
define the steady phase portion to include the first period, the second period, and the third period when the third representative flow rate varies from the first representative flow rate by less than the predetermined amount.

18. The ventilation device according to claim 17, wherein the third period immediately precedes the second period, and wherein the second period immediately precedes the first period.

19. The ventilation device according to claim 16, wherein the estimated leak flow is determined by performing an interpolation of the steady phase portion of the flow waveform.

20. The ventilation device according to claim 19, wherein the interpolation is linear regression.

* * * * *